United States Patent [19]

Coloe

[11] Patent Number: 5,281,416
[45] Date of Patent: Jan. 25, 1994

[54] SWINE DYSENTERY VACCINE

[75] Inventor: Peter J. Coloe, East Doncaster, Australia

[73] Assignee: Royal Melbourne Institute of Technology Limited, Melbourne, Australia

[21] Appl. No.: 809,202

[22] Filed: Dec. 12, 1991

Related U.S. Application Data

[63] Continuation of Ser. No. 381,417, filed as PCT/AU87/440, on Dec. 23, 1987, abandoned.

[30] Foreign Application Priority Data

Dec. 23, 1986 [AU] Australia ............... PH9632/86
Aug. 24, 1987 [AU] Australia ............... PI3940/87

[51] Int. Cl.$^5$ ................... A61K 39/02; C12N 1/00
[52] U.S. Cl. ................... 424/92; 424/88; 435/240.1; 435/243; 435/245; 435/252.1
[58] Field of Search ............ 424/92, 88; 435/240.1, 435/243, 245, 252.1

[56] References Cited

U.S. PATENT DOCUMENTS

| | | | |
|---|---|---|---|
| 4,100,272 | 7/1978 | Glock et al. | 424/92 |
| 4,152,413 | 5/1979 | Goodnow | 424/92 |
| 4,152,414 | 5/1979 | Harris et al. | 424/92 |
| 4,152,415 | 5/1979 | Harris et al. | 424/92 |
| 4,203,968 | 5/1980 | Harris et al. | 424/92 |
| 4,322,495 | 3/1982 | Kato | 435/7.22 |
| 4,418,152 | 11/1983 | Hosaka et al. | 435/7.36 |
| 4,469,672 | 9/1984 | Harris | 424/92 |
| 4,748,019 | 5/1988 | Lysons | 424/92 |
| 4,758,517 | 7/1988 | Parizek | 435/252.1 |

FOREIGN PATENT DOCUMENTS

| | | |
|---|---|---|
| 340079 | 2/1980 | Denmark . |
| 503185 | 11/1985 | Denmark . |
| 9577 | 4/1980 | European Pat. Off. . |
| 0242082 | 10/1987 | European Pat. Off. . |
| 55-047617 | 4/1980 | Japan . |
| 86/02354 | 4/1986 | PCT Int'l Appl. . |
| 86/20354 | 4/1986 | PCT Int'l Appl. ......... A61K 39/02 |
| 8405530 | 4/1984 | United Kingdom . |
| 85/03875 | 9/1985 | World Int. Prop. O. . |

OTHER PUBLICATIONS

Hudson et al, *Br. Vet. J.*, vol. 130, No. 2, pp. XXXVII-XL, 1974.
Hudson et al, *Research in Veterinary Science*, vol. 21, pp. 366-367, 1976.
Jenkins et al, *Biological Abstracts*, vol. 84, Abstract No. 28415, 1987.
Joens et al., "Enzyme-Linked Immunosorbent Assay for Detection of Antibody to *Treponema hyodysenteria* Antigens," Journal of Clinical Microbiology, Feb. 1982, pp. 249-252.
Kenna et al., "Methods for Reducing Non-Specific Antibody Binding in Enzyme-Linked Immunosorbent Assays," Journal of Immunological Methods, 85 (1985), pp. 409-419.
Pope et al., "Evaluation of the Microenzyme-Linked Immunosorbent Assay with *Treponema pallidum* Antigen," J. Clin. Microbiol. 15(4) pp. 630-634 (Apr. 1982).
Chemical Abstracts, vol. 100, No. 11, issued 1984, Mar. 12 (Columbus Ohio, U.S.A.) A. V. Golikov et al.
Chemical Abstracts, vol. 106, No. 5, issued 1987, Feb. 2 (Columbus Ohio, U.S.A.) L. A. Joens et al.

*Primary Examiner*—Michael G. Wityshyn
*Assistant Examiner*—Abdel A. Mohamed
*Attorney, Agent, or Firm*—Willian Brinks Olds Hofer Gilson & Lione

[57] ABSTRACT

Method and composition for vaccination of a pig against swine dysentary caused by T. hyodysenteriae infection characterized by parenteral, preferably intramuscular, administration to the pigs of a live strain or of an oxygen-treated, non-viable strain of T.hyodysenteriae.

19 Claims, 7 Drawing Sheets

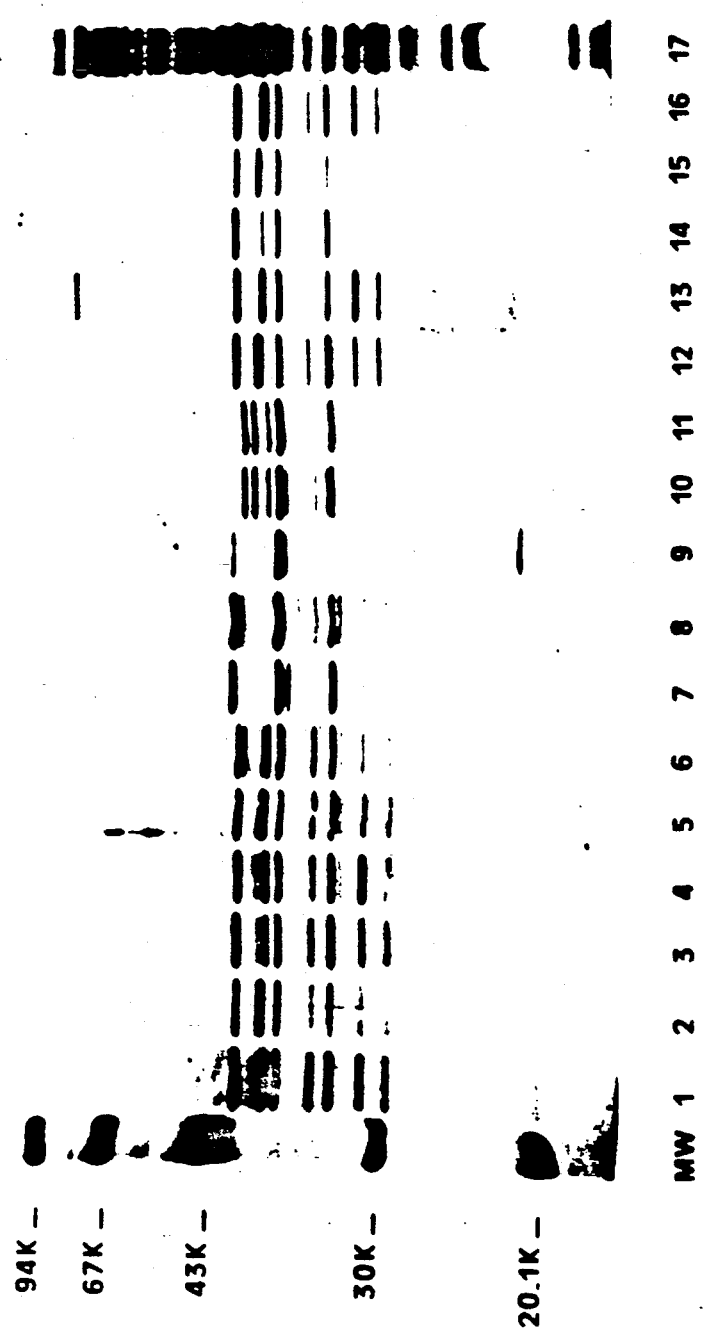

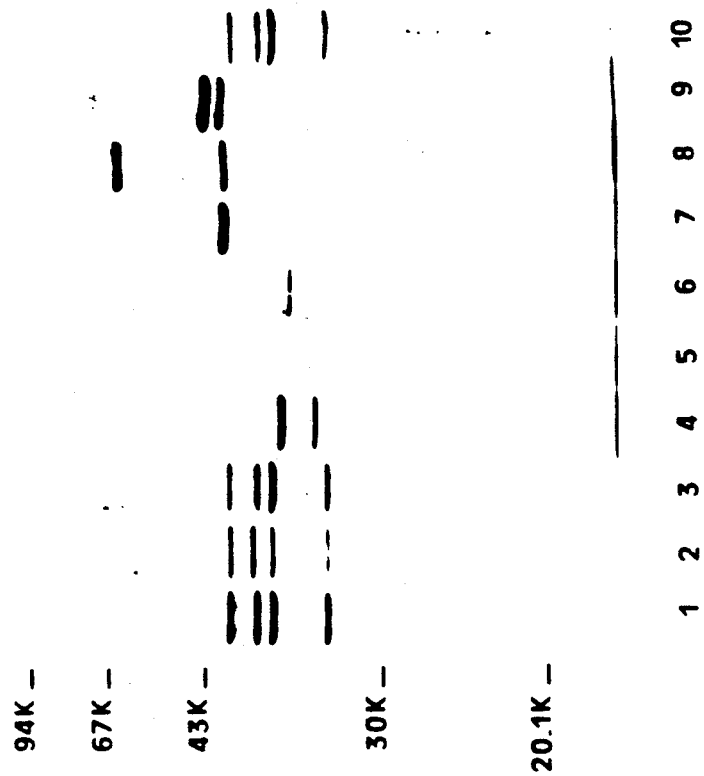

SWINE DYSENTERY VACCINE

CROSS-REFERENCE TO RELATED APPLICATIONS

This is a continuation of my application Ser. No. 07/318,417, filed as PCT/AU87/440, on Dec. 23, 1987, now abandoned.

BACKGROUND OF THE INVENTION

1. Field of the Invention

This invention relates to the immunisation of pigs against swine dysentery, and in particular it relates to a vaccine for the control of this disease.

2. Discussion of Related Art

An anaerobic spirocheate, *Treponema hyodysenteriae*, has been isolated and identified as the primary aetiological agent of swine dysentery, a mucoid, haemorrhagic diarrhoea of swine that is worldwide in distribution. The organism has a predeliction for the large intestine (colon) of swine where it proliferates, in the presence of other anaerobic bacteria, and produces a mucoid, haemorrhagic to necrotic degeneration of large portions of the large intestine. There is extensive invasion of the epithelia and lamnia propria of the tissue and the spirochaetes are clearly obvious, under light or electron microscopy, aligned along the necrotic tissue.

There is virtually no information available on the immune response of pigs to *T.hyodysenteriae* infection although it has been demonstrated that pigs that have recovered from swine dysentery are refractory to further challenge.

Several attempts have been made to develop an effective swine dysentery vaccine. U.S. Pat. No. 4,100,272 describes a vaccine comprising chemically killed cells of a virulent (pathogenic) isolate of *Treponema hyodysenteriae* for parenteral administration, whilst U.S. Pat. No. 4,152,413 describes a similar vaccine comprising killed cells of a virulent isolate for oral adminstration. U.S. Pat. Nos. 4,152,415 and 4,469,672 describe modification of the oral vaccination procedure which include the step of parenterally administering the vaccine prior to the oral administration thereof.

International Publication No. WO85/03875 discloses a modified vaccination regime which comprises parenteral administration of a priming dose of a killed vaccine, and at about the same time or thereafter the oral administration of a live, avirulent or non-pathogenic strain of *T.hyodysenteriae*.

It will be apparent that in these prior vaccination attempts, killed virulent strains of *T.hyodysenteriae* have been used and the cells have been treated with fixative chemicals such as formaldehyde. In all instances, the killed vaccine has been administered either alone by injection or orally, or by injection in conjunction will; oral administration of a killed virulent strain or a live avirulent strain. The rationale of the oral administration of the avirulent strain is to stimulate the local immunity of the large intestine, and presumably to stimulate an IgA response.

SUMMARY OF THE INVENTION

It has now been found that effective immunisation of pigs against *T.hyodysenteriae infection* can be achieved by intramuscular administration of live strains of the spirochaete. It has also been found that effective immunisation of pigs against *T.hyodysenteriae* can be achieved by intramuscular administration of oxygen-treated, non-viable strains of *T.hyodysenteriae*. Furthermore, the strains which may be used in accordance with the present invention include both virulent and attenuated strains.

According to a first aspect of the present invention, there is provided a method of vaccination of a pig against swine dysentery caused by *T.hyodysenteriae* infection characterised by parenteral, preferably intramuscular, administration to the pig of a live strain or of an oxygen-treated, non-viable strain of *T.hyodysenteriae*. As previously mentioned, either a virulent or attenuated strain of *T.hyodysenteriae* may be used in this method, and as described below, representative strains which may be used in accordance with the present invention include reference virulent strains deposited at the American Type Culture Collection under ATCC Nos.31287 and 31212, and the reference avirulent strain deposited under ATCC No.27164 (see U.S. Pat. No. 4,100,272).

BRIEF DESCRIPTION OF THE FIGURES

FIG. 2 illustrates the SDS-PAGE profiles of Sarkosyl-insoluble OM preparations, discussed in more detail below.

DETAILED DESCRIPTION OF PREFERRED EMBODIMENTS

Figure 1:
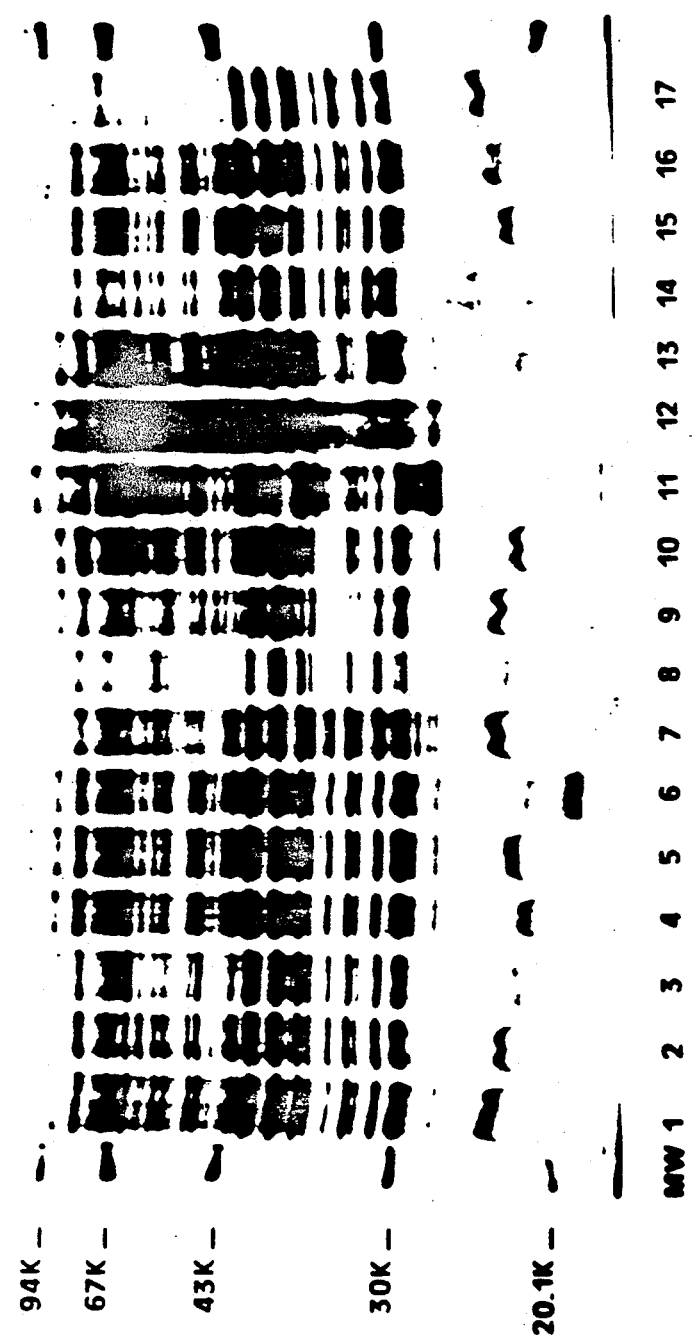
FIG. 1 illustrates SDS-PAGE profiles of whole cell lysates of isolates and reference strains of *T.hyodysenteriae*, discussed in more detail below.

The strains which can be used for parenteral, particularly intramuscular, administration in accordance with the present invention include any isolate of *T.hyodysenteriae* with a protein profile similar to the profiles of virulent strain 5380 or attenuated strain 70A including reference strains ATCC 31287, 31212 and 27164 as previously described. As described in greater detail below, minor differences in the protein profile do not appear to have a major influence on the immunogenicity of various virulent or attenuated strains, and the use of virulent strain 5380 and attentuated 70A has been described in detail herein as representative of the isolates of virulent and attenuated strains which can be used in accordance with the present invention. Outer membrane protein profiles show marked similarity of all *T.hyodysenteriae* isolates and Western blot analysis of immunogenic proteins show that antisera raised to the virulent *T.hyodysenteriae* isolate 5380 recognise immunogenic proteins in the same molecular weight region in all *T.hyodysenteriae* isolates.

No detectable differences can be observed in the protein profile of oxygenated *T.hyodysenteriae* compared to live, non-oxygenated T.hyodysenteriae. Similarly western blot analysis of immunogenic proteins shows that antisera raised to virulent T.hyodysenteriae isolate 5380 recognise the same immunogenic proteins irrespective of whether the cells have been oxygen treated or are live. The fact that the oxygen treatment results in no change in the protein profile, and hence no change in antigenicity appears to be significant, as in prior chemically killed vaccines (such as formalin-killed vaccines) it is believed that the chemical treatment destroys certain antigens including some surface antigens of T.hyodysenteriae.

In another aspect of the present invention, there is provided a vaccine composition effective in the immunisation of pigs against Treponema hyodysenteriae infection by parenteral, preferably intramuscular, administration, which comprises a live strain or an oxygen-treated, non-viable strain of T.hyodysenteriae, optionally with an adjuvant, in an acceptable carrier therefor.

The T.hyodysenteriae isolates used for preparation of the vaccine of this invention can be grown using trypticase soy broth incubated at 37°-38° C. under an anaerobic atmosphere such as 50% $H_2O$/50% $CO_2$, or 10% $CO_2$ in $N_2$. Cysteine or other reducing compounds are added to the medium to maintain anaerobiosis and, when cultures are first being grown in liquid medium, it may be necessary to supplement the medium with fetal calf serum (up to 10%), glucose, citrate, pyruvate, and iron (at 2 μg/ml of medium, crucial concentration). The liquid medium may be supplemented with spectinomycin at 400 μg/ml to suppress possible contamination with changing the protein composition of the isolated cells. If desired, the cells may then be rendered non-viable by treatment with oxygen as described below.

Alternatively, T.hyodysenteriae cells may be grown on blood agar plates under anaerobic conditions. When the cells are prepared in this manner, they must be washed in phosphated buffered saline or other isotonic solutions to remove impurities in the agar before use and then, if desired, held in oxygen saturated solution to render them non-viable.

The cultures of T.hyodysenteriae can be grown in the temperature range 35° to 42° C. and there is no difference in the protein composition of strains grown over this temperature range.

After T.hyodysenteriae cells have been grown in a fermenter they can be harvested by centrifugation and suspended in phosphate buffered saline (0.1M) or normal saline (0.1M) pH 7.0-7.4 and stored at either −70° C. or −20° C. in the concentrated form. Alternatively the cells can be aliquoted into smaller volumes and freeze dried.

To kill T.hyodysenteriae cells that have been grown in a fermentor, they are preferably oxygenated by bubbling $O_2$ gas through the medium to saturate the medium with $O_2$. The oxygenation procedure is preferably maintained for at least 3-4 hours, more preferably up to 6 hours, to render all T.hyodysenteriae in the medium non-viable. The cells can be used directly after oxygenation by combining with adjuvant or alternatively they can be harvested by centrifugation, and suspended, and stored in the concentrated form as previously described. Alternatively the cells can be aliquoted into smaller volumes and freeze dried. The cell density for vaccination should be approximately $10^9$ organisms/ml. The vaccine preferably comprises 1 ml of $1 \times 10^9$ organisms mixed with 1 ml of a suitable adjuvant, such as Freunds incomplete adjuvant (CSL). The vaccine may also include a preservative such as thimerosal. It is recommenced that the vaccine be administered by deep intramuscular injection as this procedure provides the greatest immunological response, however, other accepted methods for parenteral administration of vaccines such as subcutaneous injection may be employed, but are not preferred.

To increase the resistance of swine to T.hyodysenteriae infection it is preferable to deliver the vaccine as two (2) doses of approximately $1 \times 10^9$ T.hyodysenteriae administered 7-14 days apart. If the degree of immune response does not reach a level of greater than 1.0 OD Unit at a 1/800 dilution of serum as determined by an ELISA assay or equivalent serological assay after the second dose, a third dose of vaccine may be administered.

It is desirable in breeding stock to revaccinate animals with a yearly booster dose to maintain their IgG level above 1.00 OD Unit at a 1/800 dilution of serum.

Accompanying FIGS. 1 to 5 depict the results of an examination of the SDS-PAGE profiles of whole cell and outer-membrane (OM) enriched fractions of a number of clinical isolates of T.hyodysenteriae and reference strains ATCC 31287, 31212 and 27164.

In the Figures:

FIG. 1 shows SDS-PAGE profiles of whole cell lysates of isolates and reference strains of T.hyodysenteriae. Lanes 1 and 17, isolate strain, 70A; lane 2, isolate strain 5380; lane 3, isolate strain 5541; lane 4, isolate strain 32386; lane 5, isolate strain 32486A; lane 6, isolate strain 32486B; lane 7, reference strain ATCC 31212; lane 8, reference strain ATCC 27164; lane 9, reference strain ATCC 31287; lane 10, isolate strain 1545; lane 11, isolate strain 9690; lane 12, isolate 8841; lane 13, 8441; lane 14, isolate strain 508; lane 15, isolate strain 1059; lane 16, isolate strain 2549.

FIGS. 2A and 2B show SDS-PAGE profiles of Sarkosyl-insoluble OM preparations. FIG. 2A, 10 microgram of OM proteins from T.hyodysenteriae isolates. Lane 1, 70A; lane 2, ATCC 31287; Lane 3, ATCC 27164; lane 4, 2549; lane 5, 1545; lane 6, 5380; lane 7, 9690; lane 8, 8841; lane 9, 8441; lane 10, T.innocens 9509; lane 11, T.innocens 9510; lane 12, 1039; lane 13, ATCC 31212; lane 14, 32486B; lane 15, 508; lane 16, repeat 70A; lane 17, 5380 whole cell lysate. FIG. 2B, 10 microgram of OM proteins from T.hyodysenteriag, E.coli, S.Typhimurium, Y.enterocolitica, C.jejuni and C.fetus. Lanes 1, 2 and 3 T.hyodysenteriae isolates 70A, ATCC 31287, 5380, respectively; lane 4, E.coli JP777, lane 5; S.typhimurium V279; lane 6, Y.enterocolitica 430-1; lane 7, C.jejuni F1; lane 8, C. jejuni F14, lane 9; C. fetus subsp.fetus; lane 10, repeat 5380.

Figure 3:
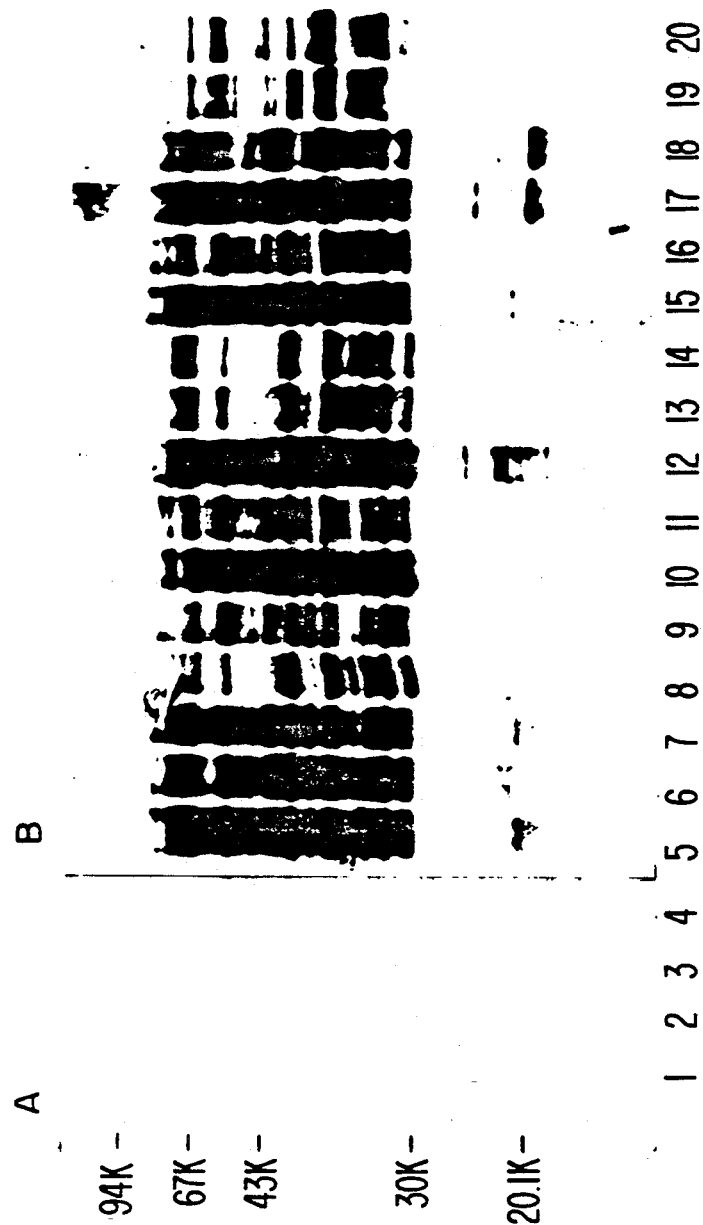
FIG. 3 illustrates results of Western immunoblot analyses of *T.hyodysenteriae* whole cell solubilized protein utilizing a specific porcine serum, discussed in more detail below.

FIG. 3 shows Western immunoblot analyses of T.hyodysenteriae whole cell solubilised proteins using specific porcine serum. Cell lysates were separated by SDS-PAGE and transferred to zetaprobe for Western blot analyses. Antigens were detected using preimmune control serum (Panel A) and polyvalent porcine anti-T.hyodysenteriae (isolate 5380) serum (Panel B) diluted 1:100. Lanes 1 and 5, 70A; lanes 2 and 6, 5380; lanes 3 and 7 ATCC, 31287; lanes 4 and 8, 32386; lane 9, 1545; lane 10, ATCC 31212; lane 11, 1059; lane 12, repeat 5380; lane 13, 5541; lane 14, 32486B; lane 15, repeat ATCC 31287; lane 16, ATCC 27164; lane 17, 9690; lane 18, 8841; lane 19, T.innocens 9510; lane 20, T.innocens 9509. Bound antibody was detected using ($^{35}$S) Protein a and subsequent autoradiography.

Figure 4:
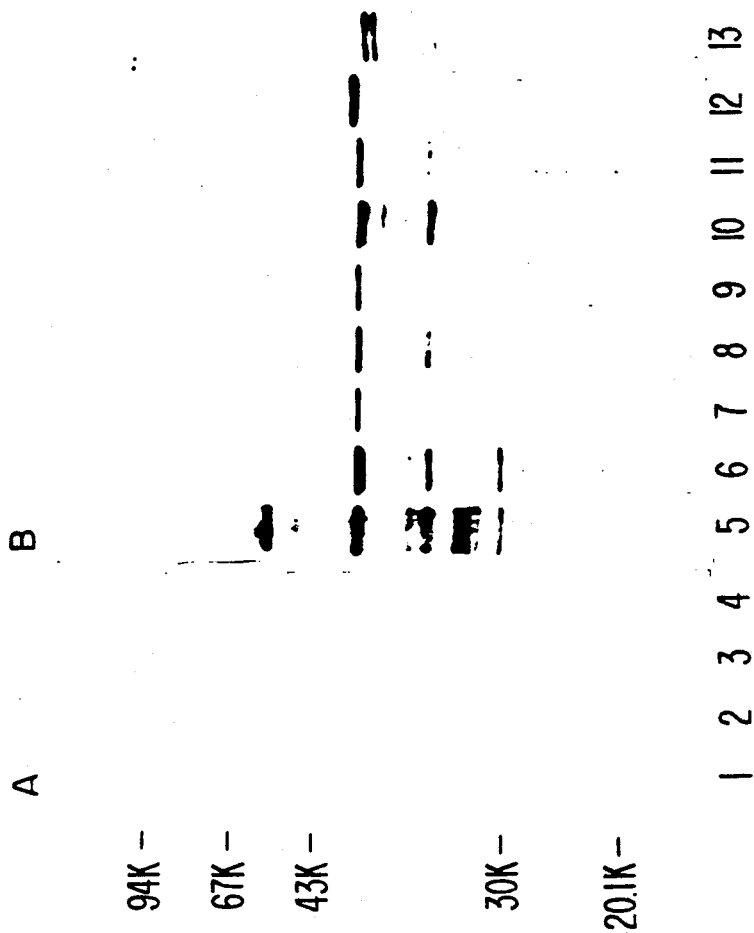
FIG. 4 illustrates results of Western blot profiles of OM proteins of *T.hyodysenteriae* isolates utilizing porcine anti-*T. hyodysenteriae* serum, discussed in more detail below.

FIG. 4 shows Western blot profiles of OM proteins of *T.hyodysenteriae* isolates using porcine anti-*T.hyodysenteriae* serum. OM proteins were prepared by Sarkosyl solubilisation. Panel A, Immune blot with pre-immune control sera; Panel B, Immune blot with hyperimmune sera. Serum was diluted 1:100. Lanes 1 and 5, *T.hyodysenteriae* 5380 cell extract; lanes 2 and 6, 5380 OMP; lanes 3 and 7, ATCC 31287 OMP; lanes 4 and 8, 70A OMP; lane 9, 2549 OMP; lane 10, 1545 OMP; lane 11, ATCC 27164 OMP; lane 12, 8841 OMP; lane 13, *T.innocens* 9510 OMP. Antibody binding was detected by incubation with ($^{35}$S)-Protein A and subsequent autoradiography.

Figure 5:
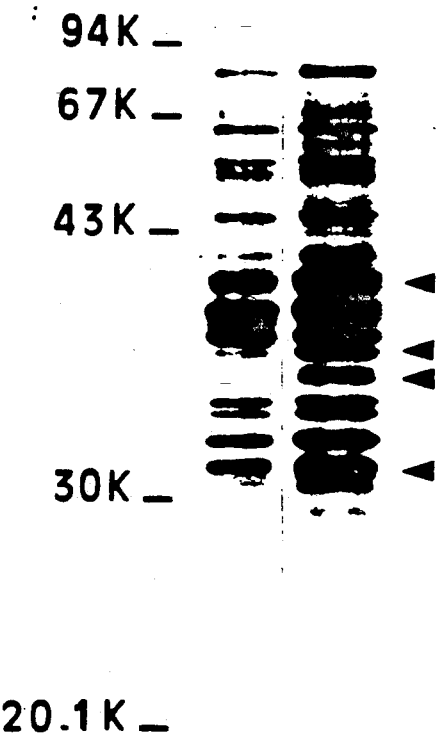
FIG. 5 shows the effect of protease digestion on *T. hyodysenteriae* isolate 5380 whole cells, discussed in more detail below.

FIG. 5 shows the effect of protease digestion on *T.hyodysenteriae* isolate 5380 whole cells. Intact cells were incubated with 50 μg/ml of trypsin (lane A) or with PBS buffer (lane B). After 30 min, reactions were stopped by the addition of PMSF and cells solubilised in SDS sample buffer prior to SDS-PAGE. Arrows indicate the position of the Coomassie blue-stained proteins sensitive to proteolysis.

RESULTS

SDS-PAGE profiles of polypeptides of whole-cell lysates from clinical isolates and type strains of *T.hyodysenteriae* showed four to seven major abundant proteins in the molecular mass (Mr) range of 30 kDa to 40 kDa and at least 30 additional less intense Coomassie blue stained proteins were resolved for each strain on SDS-PAGE. No high M.Wt. polypeptides (>200 kDa) were observed in the electrophoretic profiles. The 36 kDa and 39 kDa proteins were detected as closely migrating doublets in most isolates. In addition a diffuse band present in all strains in the M.Wt. region 22-25 kDa was identified as lipo-polysaccharide (LPS) on the basis of the silver staining and nitrocellulose binding characteristics (data not shown).

Comparison of the Coomassie blue stained protein profiles of *T.hyodysenteriae* whole-cell lysates demonstrated qualitative differences in the apparent electrophoretic mobility of the major abundant proteins migrating in the M.Wt. region of the SDS-PAGE gel between 30 kDa to 40 kDa. This strain-to-strain variability in the banding patterns could be used to differentiate two electrophoretic patterns among the isolates tested. The majority of treponemal strains examined revealed similar protein banding profiles to that of type strains ATCC 31212 and ATCC 31287 (FIG. 1, lanes 7 and 9, respectively); and were designated group A, with characteristic major abundant proteins with molecular masses of 39 kDa, 37 kDa and 36 kDa proteins. Type strain ATCC 27164 (FIG. 1, lane 8) illustrated an identical polypeptide profile to strain ATCC 31287 but did not express the 39 kDa protein doublet (also designated group A). A distinct 40 kDa protein was expressed in isolates 9690, 8841 and 8441 (FIG. 1, lanes 11, 12 and 13, respectively) and these isolates were designated group B.

Four different preparations of whole-cell lysates from the same *T.hyodysenteriae* strains (950A, 70A, 31287, 31212) were examined by SDS-PAGE after numerous passages on growth medium. All strains showed identical polypeptide profiles demonstrating that the protein composition of the isolates did not vary on passage (data not shown). Furthermore the protein profile of strain 5380 (group A (FIG. 1, lane 2) remained stable after in vivo challenge and subsequent re-isolation from several pigs (data not shown).

Cell envelope fractions from the clinical isolates and type strains of *T.hyodysenteriae* and the two isolates of *T.innocens* were extracted with Sarkosyl and Sarkosyl-insoluble, OMP-enriched preparations resolved by SDS-PAGE (FIG. 2A). The major OM proteins present in *T.hyodysenteriae* strains corresponded to the major abundant proteins migrating in the Mr range 30 kDa to 40 kDa in the cellular protein preparations (Refer to FIG. 1). The OMP profiles revealed that all group A and most group B isolates expressed-common 36 kDa, 34 kDa, 33 kDa, 31.5 kDa and 30 kDa OM proteins. Of 10 group A strains tested, 6, expressed a major 37 kDa OMP and 4 expressed a major 37.5 kDa OMP. These isolates have been designated sub-groups A1 and A2, respectively. There was no expression of the strain variable 37 kDa protein in Group B OMPs. The OMP proteins of the *T.hyodysenteriae* isolates were compared with the Sarkosyl-insoluble OMP-enriched preparations from other gram-negative bacteria (FIG. 2B). The OM patterns of *T.hyodysenteriae* isolates were readily distinguished from those of *E. coli, S. typhimurium, Y.enterocolitica, C. jejuni* and *C. fetus* subsp.fetus.

Samples of treponemal whole-cell lysates were separated by SDS-PAGE and then transferred to zetaprobe for immuno-detection. Porcine hyperimmune serum against whole *T.hyodysenteriae* strain 5380 cells (Group A) recognised at least 20 proteins with apparent molecular masses above 24 kDa, with some strain variability (FIG. 3). No proteins were recognised by the preimmune control serum. The hyperimmune porcine serum reacted strongly with a number of proteins in the molecular mass range 30 kDa to 47 kDa that were common in almost all isolates (Groups A and B) but different to the immunoreactive proteins recognised in the *T.innocens* isolates.

When Sarkosyl-insoluble OM preparations from seven *T.hyodysenteriae* (6 group A and 1 group B) isolates and a *T.innocens* isolate were separated by SDS-PAGE and immunoblotted to zetaprobe and probed with porcine anti-*T.hyodysenteriae* strain 5380 hyperimmune serum, the pattern of reactivity was similar in almost all isolates except for a small degree of strain-variation in the proteins in the 38 kDa to 40 kDa dalton molecular mass range (FIG. 4). Included for comparative purposes was the pattern of reactivity with isolate 5380 whole-cell lysate (FIG. 4), lanes 1 and 5). The OM proteins from groups A and B and the *T.innocens* isolates were reactive with antibodies present in the hyperimmune sera but not with prechallenge control serum (FIG. 4), lanes 1 to 4). In all *T.hyodysenteriae* isolates, strongly immunoreactive common OM proteins were observed at 34 kDa and 30 kDa. The 34 kDa band was also reactive in the *T.innocens* isolate (FIG. 4, lane 13). The 39 kDa band present in group A isolates (FIG. 4, lanes 6 to 11), the major 40 kDa in group B isolate 8841 (FIG. 4, lane 12) and the 38 kDa and 38.5 kDa proteins bands in the *T.innocens* isolate 9510 (FIG. 4 lane 13) were also immunoreactive. A similar antibody response was observed when OM proteins were probed with rabbit anti-*T.hyodysenteriae* hyperimmune serum (data not shown). When OM proteins from other gram-negative organisms were immunoprobed with the same porcine anti-*T.hyodysenteriae* hyperimmune serum there was no detectable antibody cross-reactivity (data not shown).

To further characterise the *T.hyodysenteriae* antigens important in the immunological response, the OM proteins recognised in the Western blots were correlated with proteins located on the surface of the *T.hyodysenteriae* Intact *T.hyodysenteriae* strain 5380 whole cells were treated with trypsin and the proteolysis stopped with PMSF. Both protease-treated and control *T.hyodysenteriae* 5380 cells were solubilised in SDS sample buffer and subjected to SDS-PAGE (FIG. 5). Trypsin proteolysis caused selective loss of the protein bands at Mr values of 39 kDa, 36 kDa, 34 kDa (doublet), and 30 kDa indicating that these proteins extend out through the OM to the treponemal cell surface. The same pattern of proteolysis was observed when proteinase K treatment of the *T.hyodysenteriae* 5380 cells was used rather than trypsin (data not shown).

Further features of the present invention are illustrated by the following experimental example.

EXAMPLE 1

A. Experimental Animals

Pigs from a property with no history of swine dysentery were placed in isolation units at 4 weeks of age and fed a grower ration containing no antibiotics. Rectal swabs were examined by dark field microscopy and inoculated onto bovine and horse blood agar with and without spectinomycin and into selenite broths. No *T.hyodysenteriae* like organisms were observed under microscopy or isolated on the isolation media. Faeces were negative for *Salmonella spp* and Compylobacter spp. All animals were negative in a *T.hyodysenteriae* ELISA assay disclosed in the copending Australian Patent Application No. PH 09631/86.

B. Vaccine Preparation

Cultures of *T.hyodysenteriae*, strains 5380 or 70A were grown for 48 hours in an anaerobically prepared Trypticase soy broth medium supplemented with cysteine, glucose, sodium citrate, sodium pyruvate, and iron, adjusted to pH 6.8, sterilized and gassed with a mixture of 10% $CO_2$ in $N_2$. Up to 10%, preferably 1%, fetal calf serum may be added to enhance growth. Cultures were harvested, and resuspended in phosphate buffered saline. The organisms were diluted to a concentration of approximately $1\times10^9$/ml before use.

C. Challenge Inoculum

Challenge inoculum consisted of the same *T.hyodysenteriae* organisms grown in liquid culture, (as above) or a single blood agar plate of the organism which had been incubated for 48 hours at 37° C.

The challenge inoculum was fed in a homogenate of 200 ml of reconstituted milk powder to pigs which had been deprived access to food for 24 hours prior to inoculation.

D. Virulence Trials

Trial 1

Four pigs were incolulated orally with the growth from 1 blood agar culture of *T.hyodysenteriae* strain 5380. The pigs were maintained on an antibiotic free diet and were monitored daily for signs and symptoms of dysentery.

The clinical response of these pigs inoculated with *T.hyodysenteriae* 5380 was as follows:

Diarrhea 4/4
Dysentery 4/4
Av.Day of onset 10 days
Av.Duration 3 days
Deaths 4/4 This trial showed that strain 5380 is virulent for pigs, and *T.hyodysenteriae* was isolated from all pigs with dysentery.

Trials 2 and 3

These were repeats of Trial 1 using six 3-week-old pigs. All pigs showed diarrhoea and dysentery 11 days post inoculation. In trial 2, two pigs died from dysentery on day 12 and the remainder, with classical signs of swine dysentery were treated with antibiotics to control the dysentery. Trial 3 results were similar.

Again these trials illustrated that strain 5380 is a virulent strain of *T.hyodysenteriae*

Trial 4

Eight pigs were challenged with cultures of 70A rather than 5380 using the same inoculation protocol as in trials 1, 2 and 3. No pigs succumbed to swine dysentery.

Trial 5

Six 4-week-old pigs were inoculated with either strain 5380 (4 pigs) or strain 70A (2 pigs) by oral inoculation of a concentrated inoculum ($1\times10^{11}$) of the *T.hyodysenteriae* strains orally and the freshly harvested surface growth from 1 agar plate intrarectecally. The pigs were housed in separate crates in the same shed and fed the same ration. All 4 pigs from the 5380 group showed evidence of clinical swine dysentery within 10 days of challenge and ½ died at 12 days. The remainder of the 5380 group were treated with antibiotics to control the dysentery. Neither of the pigs challenged with strain 70A showed any signs of dysentery up to 30 days post challenge, when the experiment was terminated.

Trial 6

Eight pigs were challenged with cultures of 70A by inoculation of 1 agar plate of actively growing *T.hyodysenteriae* 70A in milk orally and the surface growth of actively growing *T.hyodysenteriae* 70A, resuspended in 1 ml of *T.hyodysenteriae* culture broth and inoculated intrarectally. None of the pigs showed any signs of swine dysentery. However, they did show an increase in antibody titre against *T.hyodysenteriae*. *T.hyodysenteriae* could be isolated from the pig faeces in the 24 hours post inoculation. However, *T.hyodysenteriae* could not be isolated from faeces from 5 days after challenge.

E. Vaccination Trial

Trial 7

Six pigs were vaccinated intramuscularly with $2\times10^9$ *T.hyodysenteriae* 5380 in adjuvant at day 0 and revaccinated on day 11. A control group of 6 pigs, kept separately, were untreated.

All pigs were challenged at day 22 with strain 5380 challenge fed in milk as per Trial 1. All control pigs died of swine dysentery within 17 days suffering from classical swine dysentery. All vaccinated pigs were resistant to challenge and showed no evidence of *T.hyodysenteriae* infection.

Trial 8

Five pigs were vaccinated as in Trial 7 but received the second vaccination only 10 days after the initial vaccination and were then challenged on day 26 (16 days after the second vaccination) with *T.hyodysenteriae*

5380. Unvaccinated pigs began to show signs of swine dysentery within 9 days of challenge and pigs started to die of acute swine dysentery within 10 days of challenge. None of the vaccinated pigs showed any evidence of swine dysentery infection up to 45 days post challenge, T.hyodysenteriae was isolated from all infected pigs which died but was not isolated from vaccinated pigs 12 days after challenge.

The clinical response of pigs in Trial 8 was as follows:

|           | Unvaccinated | Vaccinated |
|-----------|--------------|------------|
| Diarrhoea | 5/5          | 0/6        |
| Dysentery | 5/5          | 0/6        |
| Death     | 5/5          | 1/6*       |

(*1 pig died of E. coli peritonitis. There was no evidence of T. hyodysenteriae infection in the intestine and no T. hyodysenteriae was isolated from the intestinal tissue.)

Blood was collected from all pigs in the trial and the serological titres (IgG levels) are shown in the accompanying figure (FIG. 4).

Trial 9

Because polyacrylamide gel electrophoretic analysis of the soluble cellular proteins and outer membrane proteins of T.hyodysenteriae isolates 5380 and 70A did not reveal any significant differences in their protein composition or antigenicity as determined by a western blot analysis (see FIGS. 1, 2 and 3) seven pigs were vaccinated with $2 \times 10^9$ T.hyodysenteriae 70A at day 0 and revaccinated with $2 \times 10^9$ T.hyodysenteriae 70A on day 17. Six pigs were kept separately as controls.

All pigs were challenged on day 24 (9 days after the second vaccination) with T.hyodysenteriae 5380. All control pigs showed signs of diarrhoea and dysentery, with all pigs dying of acute swine dysentery within 28 days after challenge.

None of the vaccinated pigs showed any signs of swine dysentery. One vaccinated pig did die during this trial on day 36, 12 days after challenge, with acute peritonitis. Examination of the intestinal tract did not show any evidence of swine dysentery and no T.hyodysenteriae was isolated from the large intestine. Microscopic, histological and electron microscopic analysis of unvaccinated pigs revealed changes in all pigs characteristic of acute swine dysentery—similar analysis of vaccinated pigs at the completion of the trial showed no evidence of microscopic or histological changes caused by T.hyodysenteriae infection.

Serological responses of vaccinated and unvaccinated pigs revealed marked differences in the IgG titres to T.hyodysenteriae in infected and uninfected pigs In all vaccinated pigs the serological titre (IgG) to T.hyodysenteriae was greater than 1.0 OD unit at a 1/800 dilution of serum. These vaccination trials demonstrate in pigs vaccinated with the virulent (5380) or avirulent (70A) strains of T.hyodysenteriae that an antibody titre (in excess of 1.0 at 1/800) can be obtained that will protect against challenge with a virulent strain (5380) of T.hyodysenteriae.

EXAMPLE 2

A. Experimental Animals

Pigs from a property with no history of swine dysentery were placed in isolation units at 4 weeks of age and fed a grower ration containing no antibiotics. Rectal swabs were examined by dark field microscopy and inoculated onto bovine and horse blood agar with and without spectinomycin and into selenite broths. No T.hyodysenteriae like organisms were observed under microscopy or isolated on the isolation media. Faeces were negative for Salmonella spy and Compylobacter spp. All animals were negative in a T.hyodysenteriae ELISA assay as described in copending Australian Patent Application No. PHO9631/86

B. Oxygen Treated Vaccine Preparation

Cultures of T.hyodysenteriae strain 70A were grown for 48 hours in an anaerobically prepared Trypticase soy broth medium supplemented with cysteine, glucose, sodium citrate, sodium pyruvate,, and iron, adjusted to pH 6.8, sterilized and gassed with a mixture of 10% $CO_2$ in $N_2$. Up to 10%, preferably 1%, fetal calf serum may be added to enhance growth.

Cultures were oxygenate for six hours, diluted to a concentration of approximately $1 \times 10^9$/ml, and adjuvanted before use.

C. Vaccination Trial

One hundred and ten pigs were vaccinated with oxygen-treated, non-viable, adjuvanted T.hyodysenteriae vaccine at day 0 and day 10, and 110 pigs were kept as control pigs. The pigs were all housed in a commercial piggery with endemic swine dysentery.

Unvaccinated pigs began to show signs of acute dysentery within 7 days of the vaccine trial starting. The clinical response of pigs in this vaccination trial was as follows:

|           | Unvaccinated | Vaccinated |
|-----------|--------------|------------|
| Diarrohoea | 110/110     | 2/110      |
| Dysentery | *96/110      | 1/110      |
| Deaths    | *6/110       | 1/110+     |

*All pigs showing evidence of acute dysentery were treated with 10 mg/kg Tiamulin hydrochloride once swine dysentery was detected and confirmed to reduce the deaths that would have inevitably occurred without treatment.
+One pig in the vaccinated group showed evidence of acute dysentery only 3 days after vaccination and this pig died within a few hours of the onset of the disease. It was considered that 3 days post vaccination was insufficient time to allow for the development of an adequate immune response.

Serological responses of vaccinated and unvaccinated pigs revealed marked differences in the IgG titres to T.hyodysenteriae in infected and uninfected pigs In all vaccinated pigs the serological titre (IgG) to T.hyodysenteriae was greater than 1.0 OD unit at a 1/800 dilution of serum. These vaccination trials demonstrate in pigs vaccinated with oxygen-treated, non-viable strains of T.hyodysenteriae (70A) that an antibody titre (in excess of 1.0 at 1/800) can be obtained that will protect against challenge with a virulent strain of T.hyodysenteriae.

D. Comparison of Immunogenicity

Figure 6:
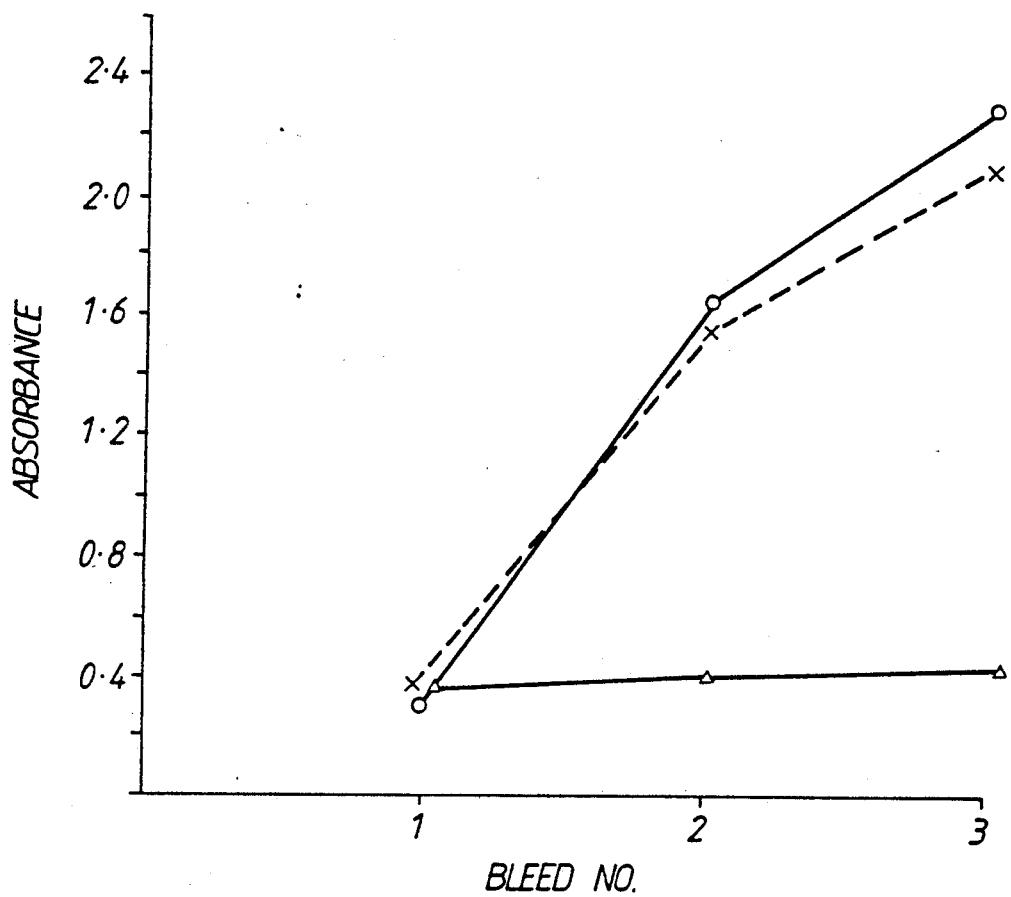
FIG. 6 is a graphical representation of results of a comparison of the immunogenicity of a live strain of the *T. hyodysenteriae* vaccine in pigs to the immunogenicity of a non-viable strain of *T.hyodysenteriae* vaccine treated with oxygen.

A comparison was made between adjuvanted live T.hyodysenteriae 70A, and adjuvanted oxygen-treated, non-viable T.hyodysenteriae 70A for ability to stimulate IgG antibodies to T.hyodysenteriae in pigs. Two doses of each vaccine, comprising $1.5 \times 10^9$ T.hyodysenteriae in adjuvant were injected intramuscularly, 10 days apart, into 2 groups of 4 pigs. A third group of 4 pigs was held as a control. Sera from all pigs were collected weekly for 3 weeks and the development of the IgG antibody titre to T.hyodysenteriae (as measured by absorbance) was recorded. The results are shown in FIG. 6. It can be seen from FIG. 6 that there is no significant difference in the absorbance figures induced by either the live or oxygen-treated vaccine.

I claim:

1. A method of vaccination of a pig against swine dysentery caused by *T.hyodysenteriae* infection, comprising the parenteral administration to the pig of an oxygen-treated, non-viable strain of *Treponema hyodysenteriae* selected from the group consisting of isolate 5380, isolates and strains of *T. hyodysenteriae* having major abundant proteins with molecular masses of 39 kDa, 37 kDa and 36 kDa, and isolates and strains of *T. hyodysenteriae* having major abundant proteins with molecular masses of 37 kDa and 36 kDa, said molecular masses being determined by SDS-PAGE gel electrophoresis of a whole cell lysate.

2. A method according to claim 1, wherein the strain of *T. hyodysenteriae* is administered by intra-muscular administration.

3. A method according to claim 1, wherein the strain of *T. hyodysenteriae* is a virulent strain.

4. A method according to claim 1, wherein the strain of *T. hyodysenteriae* is an attenuated strain.

5. A method according to claim 3, wherein prior to the administration the *T. hyodysenteriae* has been held in an oxygen saturated solution, so as to render the *T. hyodysenteriae* non-viable.

6. A method according to claim 1, wherein the strain of *T. hyodysenteriae* is selected from the group consisting of isolates and strains having characteristic major abundant proteins with molecular masses of 39 kDa, 37 kDa and 36 kDa, as determined by SDS-PAGE gel electrophoresis.

7. A method according to claim 1, wherein an adjuvant is combined with the *T. hyodysenteriae* prior to the administration thereof.

8. A method of claim 1, further comprising administering the oxygen-treated, non-viable strain of the *T. hyodysenteriae* in two doses of approximately $1 \times 10^9$ *T. hyodysenteriae*, the second dose being administered 7-14 days after the first dose.

9. A method of claim 1, comprising administering the oxygen-treated, non-viable strain of the *T. hyodysenteriae* in three doses.

10. A method according to claim 1, wherein the isolates and strains of *T. hyodysenteriae* having major abundant proteins with molecular masses of 39 kDa, 37 kDa and 36 kDa are selected from the group consisting of strains ATCC 31287, 31212 and isolate 70A.

11. A method according to claim 1, wherein the isolates and strains of *T. hyodysenteriae* having major abundant proteins with molecular masses of 37 kDa and 36 kDa is the strain ATCC 27164.

12. A parenterally administered vaccine composition effective in the immunisation of pigs against swine dysentery caused by *T. hyodysenteriae* infection which comprises an oxygen-treated, non-viable strain of *Treponema hyodysenteriae* selected from the group consisting of isolate 5380, isolates of strains of *T. hyodysenteriae* having major abundant proteins with molecular masses of 39 kDa, 37 kDa and 36 kDa and isolates and strains of *T. hyodysenteriae* having major abundant proteins with molecular masses of 37 kDa and 36 kDa, said molecular masses being determined by SDS-PAGE gel electrophoresis of a whole cell lysate, and a physiologically acceptable carrier therefor.

13. A composition according to claim 12, wherein the strains of *T. hyodysenteriae* is a virulent strain.

14. A composition according to claim 12, wherein the strain of *T. hyodysenteriae* is an attenuated strain.

15. A composition according to claim 12, wherein the *T. hyodysenteriae* strain has been held in an oxygen-saturated solution, so as to render the strain non-viable.

16. A composition according to claim 12, wherein the strain of *T. hyodysenteriae* is a strain having characteristic major abundant proteins with molecular masses of 39 kDa, 37 kDa and 36 kDa proteins, as determined by SDS-PAGE gel electrophoresis of a whole cell lysate.

17. A composition according to claim 12, further comprising Freund's incomplete adjuvant.

18. A composition according to claim 12, wherein the isolates and strains *T. hyodysenteriae* having major abundant proteins with molecular masses of 39 kDa, 37 kDa and 36 kDa are selected from the group consisting of strains ATCC 31287, 31212 and isolate 70A.

19. A composition according to claim 12, wherein the isolates and strains of *T. hyodysenteriae* having major abundant proteins with molecular masses of 37 kDa and 36 kDa is the strain ATCC 27164.

* * * * *